US006455052B1

(12) United States Patent
Marcussen et al.

(10) Patent No.: US 6,455,052 B1
(45) Date of Patent: **\*Sep. 24, 2002**

(54) ENTERIC COATING, COMPRISING ALGINIC ACID, FOR AN ORAL PREPARATION

(75) Inventors: Jørn Marcussen, Frederiksværk; Erik Brandsborg, Frederiksberg, both of (DK)

(73) Assignee: Bifodan A/S, Hundested (DK)

( \* ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/194,922
(22) PCT Filed: Jun. 6, 1997
(86) PCT No.: PCT/DK97/00252
§ 371 (c)(1),
(2), (4) Date: May 4, 1999
(87) PCT Pub. No.: WO97/46224
PCT Pub. Date: Dec. 11, 1997

(30) Foreign Application Priority Data

Jun. 6, 1996 (DK) .............................................. 0636/96

(51) Int. Cl.$^7$ .................. A61K 39/02; A61K 51/00; A61K 9/00; C12N 9/92; C12N 1/00
(52) U.S. Cl. .................. 424/234.1; 424/1.11; 424/1.13; 424/1.25; 424/1.29; 424/1.61; 424/400; 424/401; 424/439; 424/451; 424/464; 435/235.1; 435/243
(58) Field of Search .............................. 424/1.11, 1.13, 424/1.25, 1.29, 1.61, 400, 401, 439, 451, 464, 234.1; 435/235.1, 243

(56) References Cited

U.S. PATENT DOCUMENTS 3,734,987 A \* 5/1973 Hamrin
4,661,162 A 4/1987 Kurihara et al.
5,674,495 A \* 10/1997 Bowersock et al.

OTHER PUBLICATIONS

Albetshauser et al. J Control. Rel. 27:149–156, 1993.\*

\* cited by examiner

Primary Examiner—Rodney P Schwartz
(74) Attorney, Agent, or Firm—Dykema Gossett PLLC

(57) ABSTRACT

A composition for forming an enteric coating on a tablet, capsule or pellet for oral ingestion includes a liquid mixture of alginic acid particles dispersed in an aqueous solution of a binding agent of locust bean, gum, gelatine, vegetable hydrocolloids and/or animal protein.

14 Claims, No Drawings

ENTERIC COATING, COMPRISING ALGINIC ACID, FOR AN ORAL PREPARATION

This application is a U.S. national phase filing of PCT/DK97/00252, filed Jun. 6, 1997, which claimed priority of Danish Application 0636/96, filed Jun. 6, 1996.

BACKGROUND OF THE INVENTION

1. Field of the Invention

The present invention relates to a composition for forming an enteric coating on an oral preparation, such as a preparation in the form of tablets, capsules, or pellets.

2. The Prior Art

Enteric coatings are taken to mean coatings which, among other things, serve to prevent an undesired influence upon the active substance contained in the oral preparation in the stomach.

Enteric coatings are for example used for (1) preventing the gastric juice from reacting with or destroying the active substance, (2) preventing dilution of the active substance before it reaches the intestine, (3) ensuring that the active substance is not released until after the preparation has passed the stomach, and (4) preventing live bacteria contained in the preparation from being killed because of the low pH-value in the stomach.

Enteric coatings can also be used for avoiding irritation of or damage to the mucous membrane of the stomach caused by substances contained in the oral preparation, and for counteracting or preventing formation or release of substances having an unpleasant odor or taste in the stomach. Finally, such coatings can be used for preventing nausea or vomiting on intake of oral preparations.

It is known to prepare enteric coatings from one or more layers of fatty acids, such as stearic acid and palmitic acid, wax, shellac and/or cellulose acetate phthalate.

It is an essential disadvantage of the known enteric coating compositions that use of organic solvents in the form of acetone or chlorine containing compounds is required for their formation.

As regards cellulose acetate phthalates, it further applies that they must not be used for coating foodstuffs and food supplements, as they are not approved for use in foodstuffs in the EU, cf. "Fortegnoise over tilsentningsstoffer til levnedsmidier", Positivlistein, Levnedemiddelstyrelsen, December 1995, Publ. No. 231, ISSN 0903-9733, ISSN 0108-1667.

Another known enteric coating composition is acrylic resin which is available in commerce under the trade mark Eudragit®, but this coating composition also is not generally approved for formation of coatings on foodstuffs or food supplements.

JP patent publication No. 05-32543 discloses enteric coated capsules each consisting of a body and a cap containing a drug, said body and cap comprising a particulate matter such as alginic acid dispersed in an agar containing base material. The body and cap are prepared by heating an aqueous mixture of particulate material and agar containing material to about 100° C., cooling said mixture and converting the mixture into capsules by moulding.

U.S. Pat. No. 4,661,162 discloses an enteric soluble composition comprising an enteric-soluble polymer, such as carboxymethylethylcellulose, in admixture with a polyanionic polymer, such as algaric acid, which is soluble in or permeable to liquids having a pH value less than or equal to 2.

SUMMARY OF THE INVENTION

It has now surprisingly been found that a known substance, alginic acid, which has been approved for use as additive for foodstuffs, is useful for forming effective enteric coatings on oral preparations when it is combined with a binding agent.

The coating composition of the invention is characterized in that it comprises a liquid mixture of a major amount of alginic acid particles dispersed in an aqueous solution of a minor amount of a water soluble binding agent which is approved for use for coating foodstuffs and/or food supplements.

Thus, it has turned out that by forming a layer of a liquid mixture of alginic acid particles and the above-mentioned binding agent on a preparation of the form of tablets, capsules, pellets and the like, a coating is obtained which is resistant to influence of gastric juice, and which dissolves under neutral or basic conditions. This is due to the fact that alginic acid is insoluble in acids and soluble in basic or neutral media and hereby in a manner known per se forms alginate.

The best protective effect is obtained when the alginic acid particles in the mixture of alginic acid and binding agent have an average particle size of maximally 2 µm, but depending on the kind of the preparation to be provided with an enteric coating, larger and smaller particles can be used.

A particularly good protective effect is obtained by using a mixture of alginic acid particles with varying particles sizes.

As binding agent for the alginic acid particles, a wide variety of therapeutic and/or nutritionally acceptable binding agents can be employed. Preferred binding agents useful in connection with drugs as well as foodstuffs and food supplements, include locust bean gum, gelatine, vegetable hydrocolloids and animal proteins.

The liquid mixture of alginic acid particles and binding agent is aqueous, and the water preferably makes up more than 95% of the weight of the mixture. The ratio of alginic acid to binding agent may vary within wide limits depending on the binding agent, the particles size of the alginic acid, and the field of application of the coating composition.

Typically, alginic acid and binding agent are used in a weight ratio of up to 4:1.

When using an aqueous mixture of alginic agent and binding agent, such as locust bean gum, the latter is preferably dissolved in a portion of the water, and the alginic acid is slurried in the remaining portion of the water, whereafter the slurry is optionally subjected to a treatment, e.g. in a homogenizer, in order to obtain the desired particle size. Finally, the two fractions are mixed, and optionally a further homogenization is performed in order to distribute the alginic acid in the firstmentioned fraction.

The liquid mixture of alginic acid and binding agent may also contain various additives. For example, softening agent in the form of an oil, such as olive oil, and detackifiers, such as magnesium stearate, and fats may be used.

The formation of an enteric coating on an oral preparation using the coating composition according to the invention can take place in a manner known per se, e.g., by direct spraying of the liquid mixture of alginic acid and binding agent on the preparation in a fluid bed or a coating pan.

The invention also concerns a preparation provided with an enteric coating prepared by using the coating composition according to the invention.

Oral preparations which are coated with enteric coating according to the present invention are particularly suitable for containing live organisms, such as freeze-dried bacteria.

Further, the invention relates to a process for the preparation of an enteric coating on an oral preparation containing live organisms, which process does not employ toxic organic solvents, and in which the temperature does not exceed about 30° C.

When coating an oral preparation containing live organisms, e.g. freeze-dried bacteria, it is important that the bacteria are not exposed to extraneous influences which may entail that the bacteria are damaged or at worst die.

Use of toxic organic solvents and high temperatures in the preparation of enteric coatings on the oral preparation should consequently be avoided. In the present invention for the preparation of enteric coatings on the oral preparation, the temperature preferably does not exceed about 30° C. Further, no toxic organic solvents are used.

In a further embodiment of the process according to the present invention, the oral preparation which is coated with the enteric coating is constituted by capsules, preferably gelatine capsules. If a preparation in the form of capsules is used, also a gentle preparation of the active substance is obtained prior to it being coated with the enteric coating, as the physical conditions during the preparation of the capsules do not influence the active substance. The active substance, e.g. in the form of freeze-dried bacteria, is filled into empty capsules, as opposed to tablets and pellets where the active substance participates in the preparation of the tablet or pellet.

The enteric coating has turned out to be particularly effective for capsules of gelatine.

Depending on the kind of the preparation, it may be desirable to build the enteric coating from several layers, one of which is constituted by fine grained alginic acid particles bonded by a binding agent.

For example, it may be desirable to prepare a coating consisting of four layers, where one of the centre layers is prepared from the coating composition according to the invention.

It may also be desirable to provide an inner layer consisting of several sub-layers. Similarly, the outer layer may be built from several layers.

In the following the invention is described in more detail, reference being made to the following example.

EXAMPLE

For use in the preparation of an enteric coating on gelatine capsules containing freeze-dried lactic acid bacteria, the following three coating compositions are employed:

| Coating composition 1 | |
|---|---|
| Zein F-4000 | 10% |
| Ethyl alcohol 96% | 79% |
| Purified water | 9% |
| Magnesium stearate | 2% |

Coating composition 1 was prepared by slurrying Zein F-4000 in ethyl alcohol, whereafter the magnesium stearate was admixed. Finally, the water was admixed with stirring.

| Coating composition 2 | |
|---|---|
| Sodium alginate | 2.7% |
| Purified water | 97% |
| Olive oil | 0.15% |
| Magnesium stearate | 0.15% |

Coating composition 2 was prepared by dissolving sodium alginate in the water, whereafter the olive oil and the magnesium stearate were added and homogenized by means of a homogenizer.

| Coating composition 3 | |
|---|---|
| Alginic acid | 1.5% |
| Locust bean gum | 0.8% |
| Olive oil | 0.8% |
| Purified water | 96.9% |

Coating composition 3 was prepared by dissolving 0.8 parts of locust beam gum in 38.4 parts of water, whereafter 0.8 parts of olive oil were added, and the mixture was emulsified with a homogenizer. 1.5 parts of alginic acid were slurried in 58 parts of water and homogenized with a homogenizer, whereafter the above olive oil emulsion was added, and the mixture was homogenized with a homogenizer.

The coating compositions used were applied onto the gelatine capsules in the order and under the conditions stated in Table 1 below.

TABLE 1

| Process | Coating composition | Amount of liquid, g | Nozzle diameter | Nozzle pressure | Spray speed | Starting temperature | Post-drying min. | Post-drying min. | Water activity in capsule |
|---|---|---|---|---|---|---|---|---|---|
| Preheating | 0 | 0 | | | | 30° C. for 15 min. | | | 0.198 before process |
| Pretreatment | Ethanol 96% | 1500 g | 0.8 mm | 0,8 bar | 60 g/min. | 30° C. | 30° C. | 0 | 0.162 after process |
| 1st | 1 | 5000 | 0.8 mm | 0.8 bar | 60 g/min. | 30° C. | 30° C. | 15 min. | 0.218 after process |
| Layer | 2 | 5000 | 1.2 mm | | 60 g/min. | | | | |
| 2nd Layer | 3 | 5000 | 1.2 mm | 0.8 | 60 g/min. | 30° C. | 30° C. | 10 min. | 0.218 after process |
| 3rd | 1 | 1000 | 0.8 mm | 0.8 bar | 60 g/min. | 30° C. | 30° C. | 0 | |
| Layer | 2 | 1000 | 1.2 mm | | 60 g/min. | | | | |
| 4th Layer | 1 | 700 | 0.8 mm | 0.8 bar | 60 g/min. | 30° C. | 30° C. | 15 min. | |
| Cooling | 0 | | | | | up to 22° C. | - heat | up to 22° C. | 0.209 after process |

As appears from the table above, the water activity in the capsules (measured by means of a "Novasina"-moisture meter) does not increase significantly in spite of aqueous coating compositions having been used. This is very important for the stability of many substances and for the survival of freeze-dried bacteria.

The finished capsules were tested in accordance with European Pharmacepoeia: 6 capsules are exposed to the influence of 0.1N hydrochloric acid at 37° C. for 2 hours in European Pharmacepoeia's decay apparatus and must show no signs of dissolution or disruption which allows the content to escape. Thereafter, the acid is replaced by a phosphate buffer solution with pH 6.8. After 60 min, the capsules must have dissolved.

The film coated capsules stood up to this test and had all dissolved after 18 min in the phosphate buffer.

For the purpose of clarifying the stability of lactic acid bacteria containing preparations provided with an enteric coating according to the invention, decay experiments were performed in which the number of micro-organisms contained in enterically coated capsules were counted, before and after treatment with 0.1N HCl for 2 hours, and at 36–38° C. in accordance with Ph. Eur. 2nd Ed., 478, 1990.

The results of these decay experiments appear from Tables 2–5.

TABLE 2

| Sample No. | Number of live lactobacillus pr. gram of MRS agar 37° C.-3 days, $CO_2$-atomosphere |
| --- | --- |
| 1 a | $7.0 \times 10^7$ |
| 1 b | $5.8 \times 10^7$ |
|  | Mean value: $6.8 \times 10^7$ |
| 2 a | $7.3 \times 10^7$ |
| 2 b | $6.9 \times 10^7$ |

TABLE 3

| Sample No. | Number of live bifidobacteria pr. gram of RCM agar 37° C.-5 days, anaerobic |
| --- | --- |
| 1 a | $4.0 \times 10^8$ |
| 1 b | $3.9 \times 10^8$ |
|  | Mean value: $4.0 \times 10^8$ |
| 2 a | $3.8 \times 10^8$ |
| 2 b | $4.4 \times 10^8$ |

TABLE 4

| Sample No. | Number of live lactobacillus pr. gram of MRS agar 37° C.-3 days, $CO_2$-atmosphere |
| --- | --- |
| 1 a | $2.0 \times 10^7$ |
| 1 b | $1.4 \times 10^7$ |
|  | Mean value: $2.7 \times 10^7$ |
| 2 a | $3.0 \times 10^7$ |
| 2 b | $4.5 \times 10^7$ |

TABLE 5

| Sample No. | Number of live bifidobacteria pr. gram of RCM agar 37° C.-5 days, anaerobic |
| --- | --- |
| 1 a | $1.7 \times 10^7$ |
| 1 b | $1.5 \times 10^7$ |
|  | Mean value: $2.0 \times 10^7$ |
| 2 d | $2.2 \times 10^7$ |
| 2 b | $2.5 \times 10^7$ |

As appears from the above results, the acid treatment only results in a negligible drop in live micro-organisms.

What is claimed is:

1. A composition for formation of an enteric coating on an oral preparation, comprising a liquid mixture of alginic acid particles dispersed in an aqueous solution of a water soluble binding agent selected from the group consisting of locust bean, gum, gelatine, vegetable hydrocolloids and animal proteins, said liquid mixture containing a larger amount of alginic acid particles than water soluble binding agent.

2. A composition according to claim 1, characterized in that the alginic acid particles have an average particle size of 2 µm.

3. A composition according to claim 1, wherein the alginic acid particles have varying particle sizes.

4. A composition according to claim 1, wherein the alginic acid particles and the binding agent are present in a weight ratio of up to 4:1.

5. A process of preparing a coated oral preparation, comprising spraying the oral preparation with a coating composition according to claim 1 and allowing the water to evaporate.

6. A process according to claim 5, wherein the oral preparation contains live bacteria.

7. A process according to claim 5, wherein the oral preparation is in the form of capsules.

8. A process according to claim 7, wherein said oral preparation is in the form of a gelatine capsule.

9. An oral preparation provided with an enteric coating, proposed from a liquid mixture of alginic acid particles dispersed in an aqueous solution of a water soluble binding agent selected from the group consisting of locust bean, gum, gelatine, vegetable hydrocolloids and animal proteins, said liquid mixture containing a larger amount of alginic acid particles than water soluble binding agent.

10. An oral preparation according to claim 9, further including live bacteria.

11. An oral preparation according to claim 10, wherein said live bacteria are freeze dried.

12. An oral preparation according to claim 9, in the form of tablets, capsules or pellets.

13. An oral preparation according to claim 12, wherein said oral preparation is in a gelatine capsule.

14. An enterically coated oral preparation comprising alginic acid particles dispersed in a matrix of a water-soluble binding agent selected from the group consisting of locust, bean, gum, gelatine, vegetable hydrocolloids, and animal proteins, said liquid mixture containing a larger amount of alginic acid particles than water soluble binding agent.

* * * * *

UNITED STATES PATENT AND TRADEMARK OFFICE
CERTIFICATE OF CORRECTION

PATENT NO. : 6,455,052 B1
DATED : September 24, 2002
INVENTOR(S) : Jørn Marcussen et al.

It is certified that error appears in the above-identified patent and that said Letters Patent is hereby corrected as shown below:

<u>Column 6,</u>
Lines 19-20, change "locust bean, gum" to -- locust bean gum --

Signed and Sealed this

Third Day of June, 2003

JAMES E. ROGAN
*Director of the United States Patent and Trademark Office*